United States Patent [19]

Sakairi et al.

[11] Patent Number: 5,103,093

[45] Date of Patent: Apr. 7, 1992

[54] MASS SPECTROMETER

[75] Inventors: Minoru Sakairi, Kawagoe; Hideki Kambara, Hachioji, both of Japan

[73] Assignee: Hitachi, Ltd., Tokyo, Japan

[21] Appl. No.: 343,363

[22] Filed: Apr. 26, 1989

[30] Foreign Application Priority Data

Apr. 27, 1988 [JP] Japan .................................. 63-102508

[51] Int. Cl.[5] ............................................. H01J 49/28
[52] U.S. Cl. ...................................... 250/288; 250/281
[58] Field of Search ............... 250/288 A, 288 R, 281, 250/282

[56] References Cited

U.S. PATENT DOCUMENTS

| 4,531,056 | 7/1985 | Labowsky et al. | 250/288 |
|---|---|---|---|
| 4,542,293 | 9/1985 | Fenn et al. | 250/288 |
| 4,667,100 | 5/1987 | Lagna | 250/281 |
| 4,769,540 | 9/1988 | Mitsui et al. | 250/288 |
| 4,794,252 | 12/1988 | Bateman et al. | 250/288 |
| 4,808,819 | 2/1989 | Hirose | 250/288 |
| 4,814,612 | 3/1989 | Vestal et al. | 250/288 |
| 4,842,701 | 6/1989 | Smith et al. | 250/288 |
| 4,861,988 | 8/1989 | Henion et al. | 250/281 |
| 4,888,482 | 12/1989 | Kato | 250/288 |
| 4,902,891 | 2/1990 | Vestal | 250/282 |
| 4,960,992 | 10/1990 | Vestal | 250/288 |

OTHER PUBLICATIONS

Sakairi et al., "Characteristics of a Liquid Chromatograph/Atmospheric Pressure Ionization Mass Spectrometer", Analytical Chemistry, vol. 60, No. 8, Apr. 15, 1988, pp. 774-780.

Primary Examiner—Jack I. Berman
Assistant Examiner—Kiet T. Nguyen
Attorney, Agent, or Firm—Antonelli, Terry, Stout & Kraus

[57] ABSTRACT

A mass spectrometer which comprises an ion source for ionizing a sample and a mass analyzing region for introducing the thus formed ions into a vacuum and mass analyzing the ions, the ion source being provided with a spray ion source comprising a heatable capillary working at least under the atmospheric pressure, the center axis of the capillary being aligned along the center of an aperture for withdrawing the ions and the tip end of the capillary being positioned close to the aperture ionizes a sample from a liquid chromatograph by both atmospheric pressure ionization mode and a thermospray ionization mode and mass analyze the ions, thereby obtaining more exact analytical information on the sample.

7 Claims, 16 Drawing Sheets

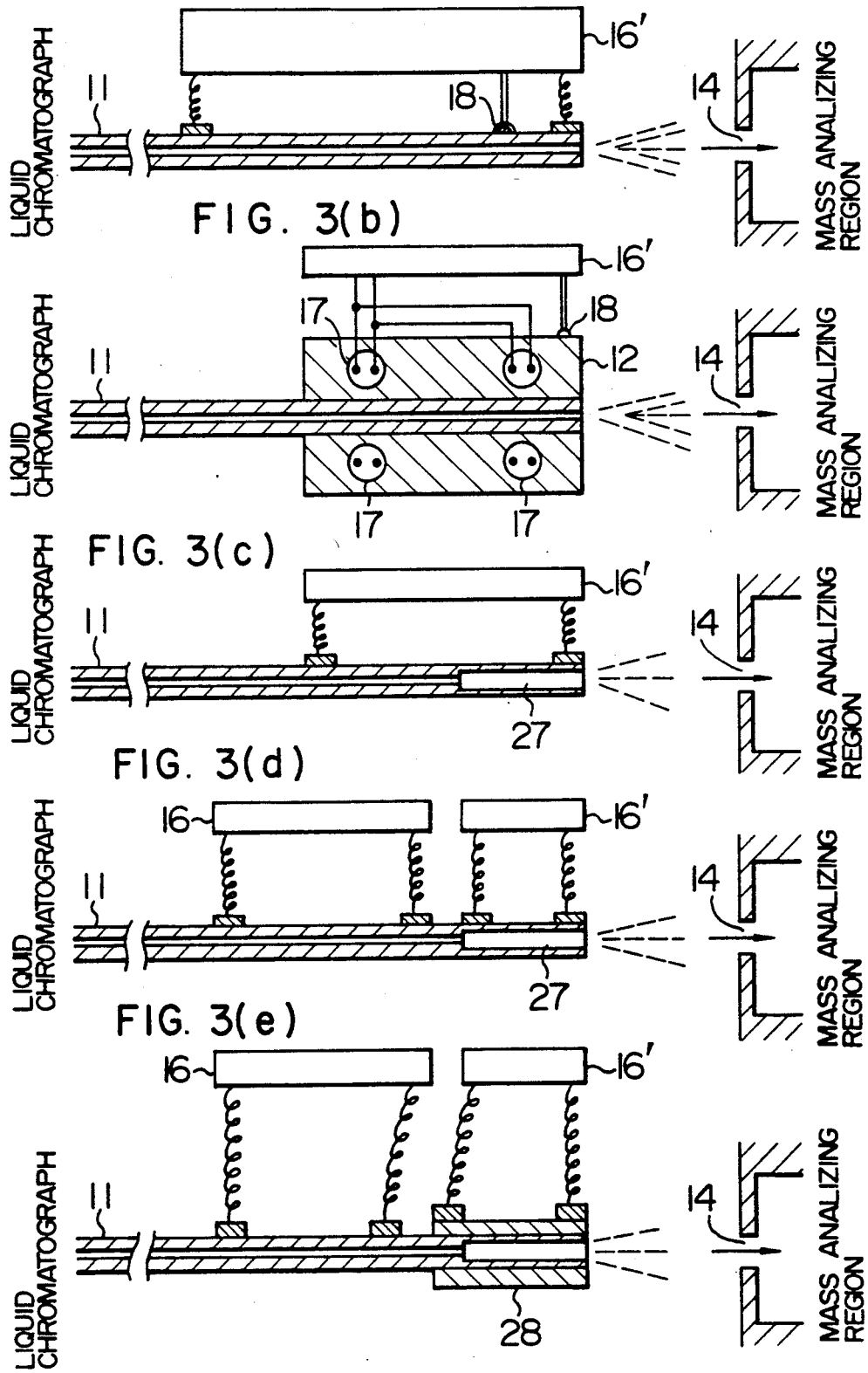

FIG. 5(a)
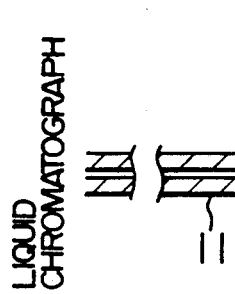 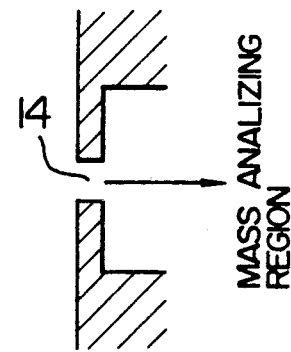
FIG. 5(b)
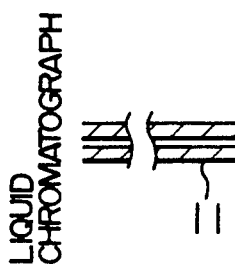 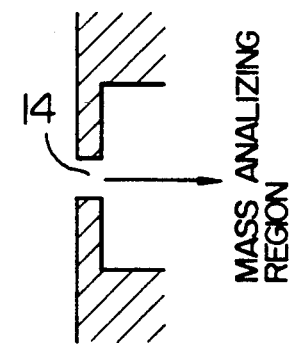
FIG. 5(c)
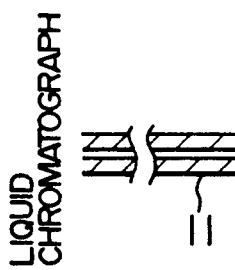 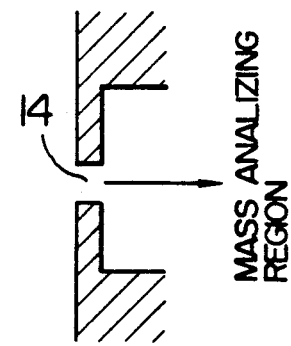
FIG. 5(d)
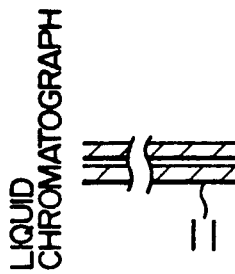 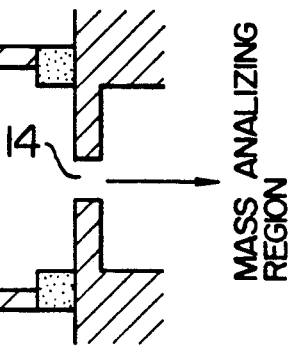

MASS SPECTROMETER

BACKGROUND OF THE INVENTION

This invention relates to a mass spectrometer, and more particularly to a liquid chromatograph-coupled mass spectrometer, that is, liquid chromatograph/mass spectrometer, suitable for separating and analyzing a broad range of important non-volatile compounds in a living body, such as amines, amino acids, steroids, antibiotics, sugars, peptides, vitamins, etc.

Now, development of separation and analyzing techniques for the compounds relating to the living body is one of the important tasks in the analytical field. To this end, a liquid chromatograph having a distinguished separation ability coupled with a mass spectrometer having a distinguished identification ability has been under extensive development.

In FIG. 11, an entire structure of liquid chromatograph/mass spectrometer, where a double focusing mass spectrometer containing an electric field analyzing section 4 and a magnetic field analyzing section 5 is used in the mass analyzing region is shown to help understand the working principle of the liquid chromatograph/mass spectrometer.

A sample in the solution, separated by and eluted from a liquid chromatograph 1 is introduced into an ion source 3 through a line 2. Ions of sample molecules formed in the ion source 3 are introduced into a vacuum through an aperture and further into a mass analyzing region comprising an electric field analyzing section 4 and a magnetic field analyzing section 5 and mass analyzed. The mass analyzed ions are detected by an ion detector 6 and the detected information is led to a data processing section 7. The mass analyzing region comprising the electric field analyzing section 4 and the magnetic field analyzing section 5 is evacuated by an appropriate pumping system 9. Numeral 8 is a power source for the ion source 3, and numeral 10 is a signal transmission line. The working principle itself of a liquid chromatograph/mass spectrometer is simple, as described above, but the liquid chromatograph handles a sample in a liquid solution state, whereas the mass spectrometer handles a sample in a gaseous state. That is, there is an incompatibility therebetween, and thus the development of liquid chromatograph/mass spectrometer is a very difficult problem.

In order to solve the difficult problem, several methods have been proposed, typical of which are an atmospheric pressure ionization method disclosed in Japanese Patent Application Kokai (Laid-open) No. 60-127453 and a thermospray method disclosed in Analytical Chemistry, Vol. 55, No. 4, April, 1983, pp. 750–754.

As shown in FIG. 12, the atmospheric pressure ionization method comprises nebulizing solutions eluted from a liquid chromatograph by nebulization by means of a heated capillary 11 or by ultrasonic nebulization, further heating the nebulized solutions by a heated block 12, thereby vaporizing the nebulized solutions, ionizing the vaporized sample molecules by corona discharge by means of a needle electrode 13 and by a series of successive ion-molecule reactions, introducing the thus formed ions into a vacuum through a first aperture 14 and a second aperture 15 and mass analyzing the ions. The atmospheric pressure ionization method is characteristic of a high sensitivity and easy coupling with a liquid chromatograph because the ion source works under the atmospheric pressure. Intense molecular ions can be obtained from low-polar amines, steroids, antibiotics, etc. among the important, non-volatile compounds in the living body and can be mass analyzed, but molecular ions are less obtainable from high-polar sugars and peptides and are hard to mass analyze.

On the other hand, as shown in FIG. 13, the thermospray method comprises spraying solutions containing both samples and buffers like ammonium acetate from a heated capillary 11' into a vacuum of a few Torr or less, introducing ions formed by vaporization of the thus formed droplets into a mass analyzing region through a second aperture 15 and mass analyzing the ions in the mass analyzing region. In contrast to the atmospheric pressure ionization method, the thermospray method can analyze high-polar compounds such as sugars and peptides, but low-polar compounds such as amines, steroids, antibiotics, etc. are hard to analyze.

Thus, it seems that a broad range of important compounds relating to the living body can be analyzed by developing a liquid chromatograph/mass spectrometer provided with such two ion sources. A combined ion source having an ionization function based on such two ion sources seems to have such a structure, for example, as shown in FIG. 14. However, the following new problems are brought about by the essential difference between the atmospheric pressure ionization method working under the atmospheric pressure and the thermospray method working under a pressure as low as a few Torr.

1) The structure of combined ion source is complicated, because when the atmospheric pressure ionization method is used, a valve (not shown in the drawing) must be provided so that no liquid may leak out of a capillary 11' used in the thermospray method, whereas when the thermospray method is used, a valve (not shown in the drawing) must be provided so that no gas may leak out of an aperture for introducing the ions formed by the atmospheric pressure ionization method.

2) The atmospheric pressure ionization method requires no liquid nitrogen trap, etc. to prevent the pumping system from contaminations due to the eluate from the liquid chromatograph, whereas the thermospray method requires the trap (not shown in the drawing) and continuous analyzing operation must be discontinued to wash the trap at intervals of a few hours.

3) In case of the thermospray method, the inside of the ion source is always exposed to a large volume of gas and thus has a high chance for the contamination.

SUMMARY OF THE INVENTION

An object of the present invention is to provide a liquid chromatograph/mass spectrometer having a novel ion source, into which the ion source of the atmospheric pressure ionization method and the ion source of the thermospray method are integrated, and which are free from the foregoing problems.

The object of the present invention can be attained by making the ion source of the thermospray method workable under the atmospheric pressure and integrating the ion source of the thermospray method with that of the atmospheric pressure ionization method.

However, most of ions formed by the thermospray method cannot be introduced into the mass analyzing region simply by increasing the working pressure of the ion source of thermospray method from a few Torr to the atmospheric pressure, as shown in FIG. 15, and the mass spectrometer does not work properly, because the amount of ions moving into the vacuum through apertures 14 and 15 are extremely decreased by the thermospray method in the structure as shown in FIG. 15.

In a method for generating ions by spraying solutions under the atmospheric pressure, a process for nebulization and vaporization by heating and a process for ionization take place in parallel, and it is preferable in that method to generate ions at the tip end of capillary, because neutralization of ions does not take place at the inside wall of capillary. Furthermore, radial distribution of an ion stream obtained by spraying solutions under the atmospheric pressure from the capillary is higher near the capillary center axis and much smaller toward the peripheral side. As shown in FIG. 16, most of the ions cannot be introduced into the mass analyzing region through the apertures in such a structure that the capillary is provided in parallel to the apertures as in the conventional ion source of thermospray method.

In the present invention, the capillary tip end can be heated and temperature-controlled, independently of the remaining part of the capillary and the center axis of the capillary is so arranged as to align along the center of apertures even in case of the thermospray method. The thus obtained jet is in a thoroughly vaporized state and can be used as such in the atmospheric pressure ionization method.

Polar components in the eluate from the liquid chromatograph are ionized by spraying the eluate from the metallic capillary, and the thus formed ions are moved through apertures, sampled and mass analyzed.

Less polar components are ionized by corona discharge at a discharge electrode such as a needle, etc. and by a series of successive ion-molecule reactions and mass analyzed. Thus, components having various chemical properties can be ionized and analyzed in the present invention.

DESCRIPTION OF PREFERRED EMBODIMENTS

Embodiments of the present invention will be described below, referring to FIGS. 1 to 11 and a system using a double focusing mass spectrometer comprising an electric field analyzing section 4 and a magnetic field analyzing section 5. Needless to say, other types of mass spectrometers such as a quadrupole mass spectrometer, etc. can be also used in the present invention.

Figure 1:
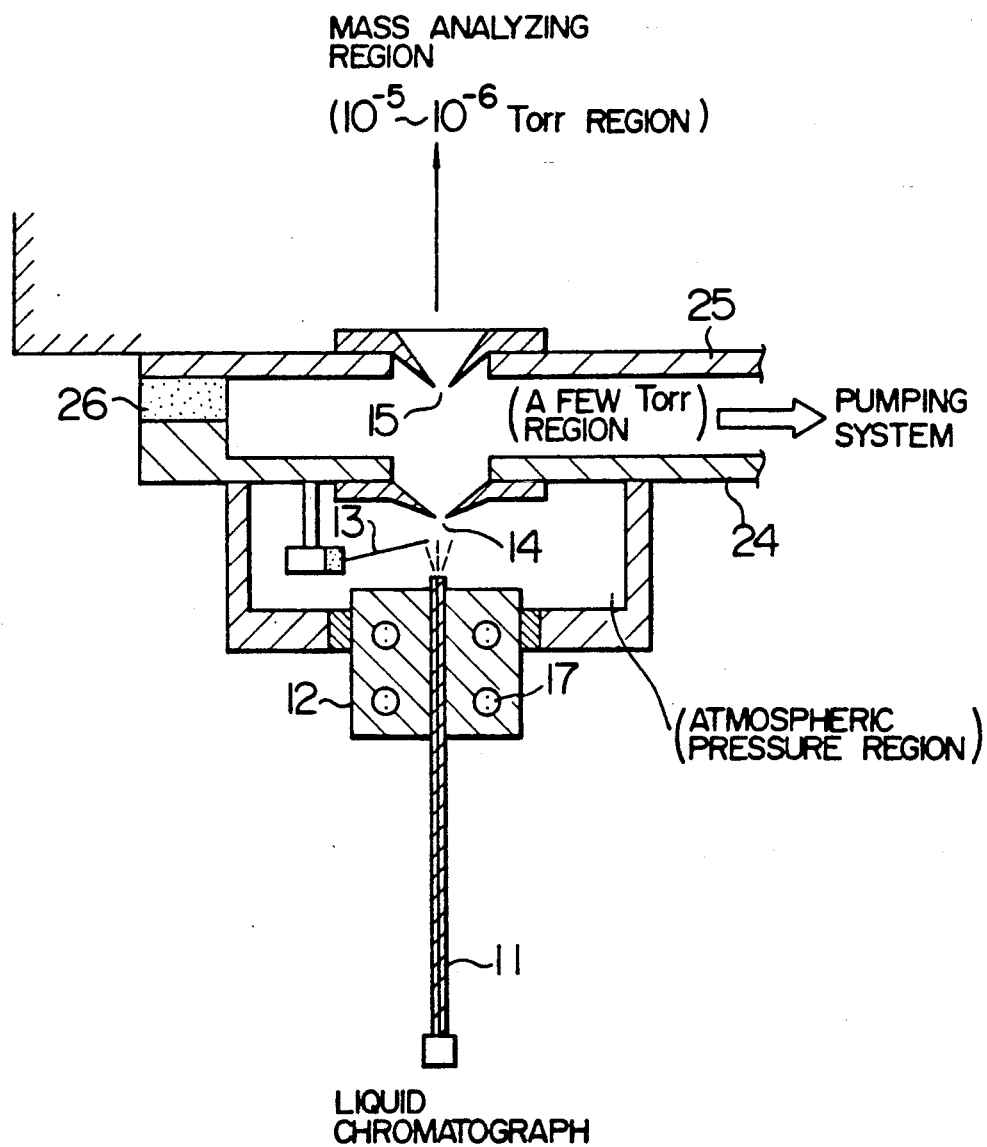
FIG. 1 is a schematic view showing the structure of the ion source of a mass spectrometer according to one embodiment of the present invention.

In FIG. 1, the structure of an ion source according to one embodiment of the present invention is shown.

Figure 2A:
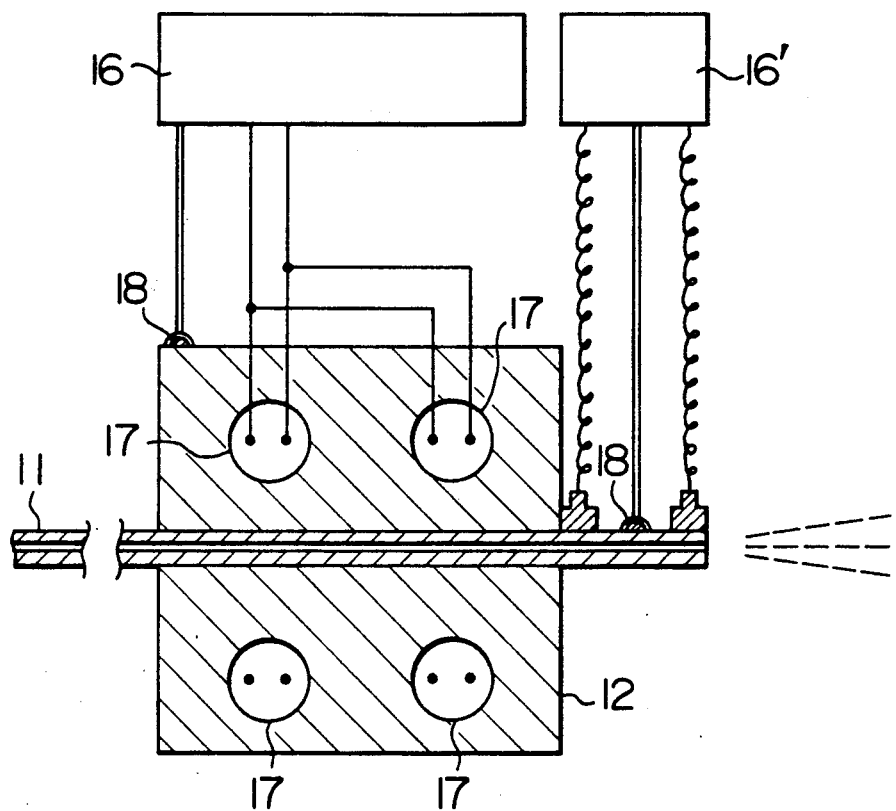
FIGS. 2(a-b) and 3(a-e) are views showing a method for heating a metallic capillary.
Figure 2B:
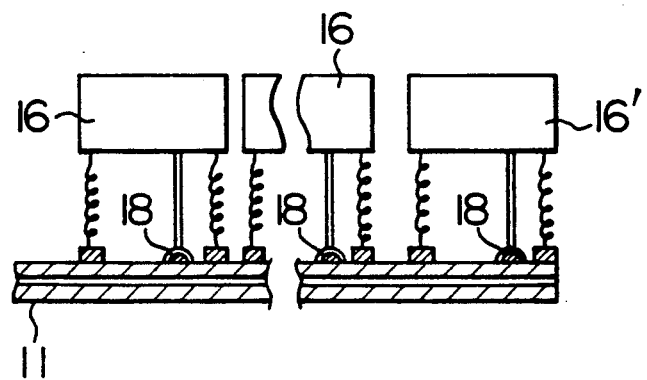
Figure 4A:
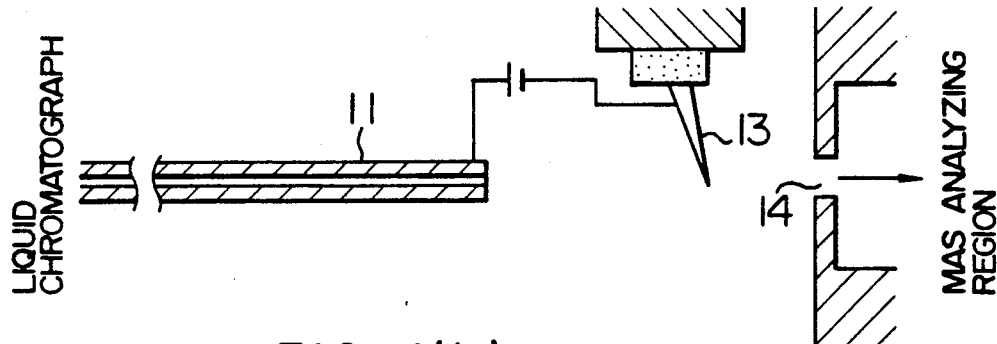
FIGS. 4(a-d) and 5(a-d) show embodiments of corona discharge electrode.
Figure 4B:
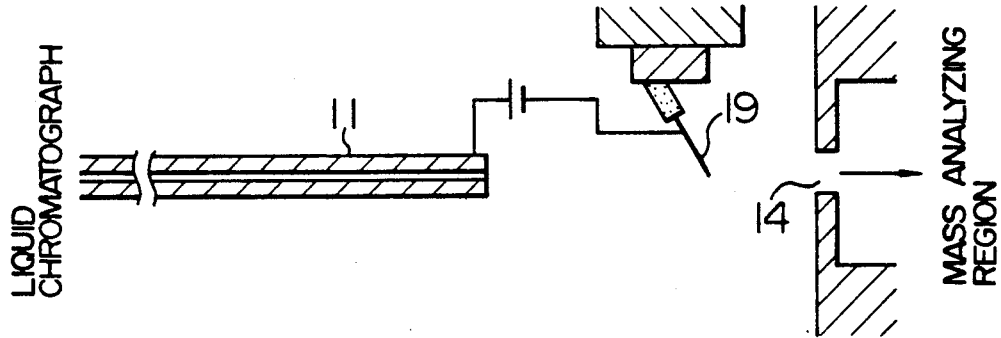
Figure 4C:
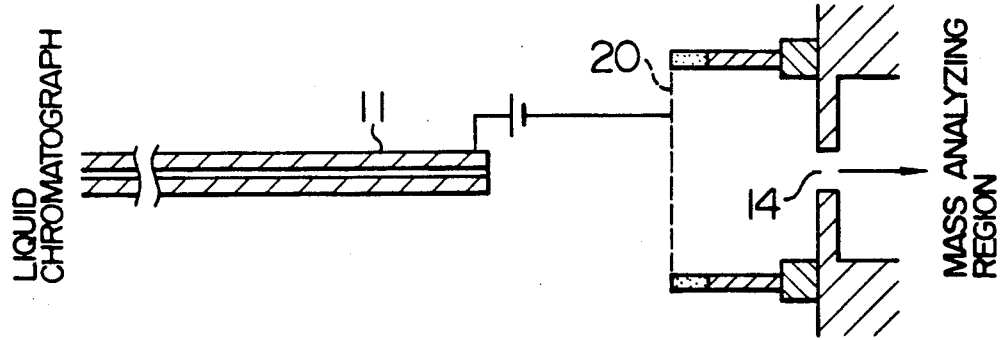
Figure 4D:
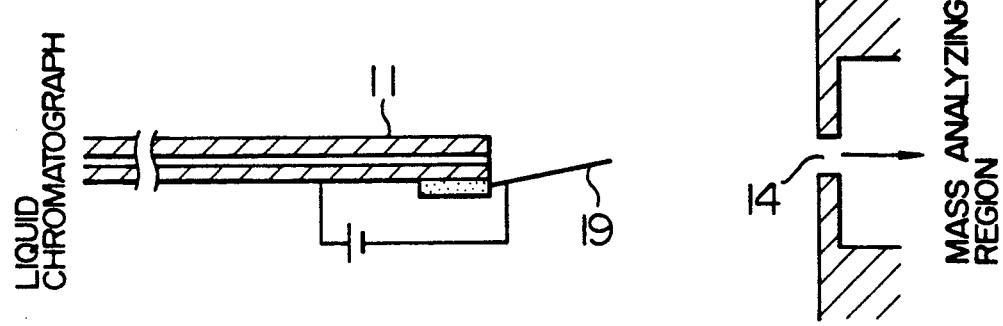

A sample in solution separated by a liquid chromatograph and eluted from the liquid chromatograph is introduced into a metallic capillary 11 with a connector through a line 2. The metallic capillary 11 can be heated and temperature-controlled. The metallic capillary 11 is indirectly heated as a whole by heating cartridge heaters 17 embedded in a metallic block 12 through a heating power source 16. In order to heat the tip end part of metallic capillary 11 particularly, the tip end part of metallic capillary 11 is directly electrically heated by an appropriate auxiliary power source 16', as shown in FIG. 2(a). An increase in the amount of ions is observable by separately heating the tip end part. In this embodiment, a combination of indirect heating of capillary 11 as a whole and direct heating of tip end part is used, but it is also possible to indirectly or directly heat both of capillary 11 as whole and the tip end part. Furthermore, in order to heat the metallic capillary 11 fully, the metallic capillary 11 is divided into a plurality of parts and the individual parts can be heated separately as shown in FIG. 2(b). Still furthermore, it is also possible to electrically directly heat only one part of tip end [FIG. 3(a)] or indirectly heat the part [FIG. 3(b)], though the amount of ions generated through spraying is decreased, as compared with that of the aforementioned two procedures of FIGS. 2(a) and (b).

In order to suppress a pressure increase on the inside of capillary due to partial vaporization to some extent of solution by heating, the inner diameter can be a little enlarged at the tip end part of capillary to be heated [FIGS. 3(c) and (d)], or another capillary 28 having a little larger diameter can be connected to the capillary 11 and heated [FIG. 3(e)]. In any of these cases, a thermocouple 18 is provided on the metallic capillary 11 or metallic block 12 to monitor and control the temperature.

The eluate from the liquid chromatograph 1 is heated and vaporized through the metallic capillary 11 heated by the foregoing heating procedure, and a portion of the vapor is discharged as ions.

Figure 6:
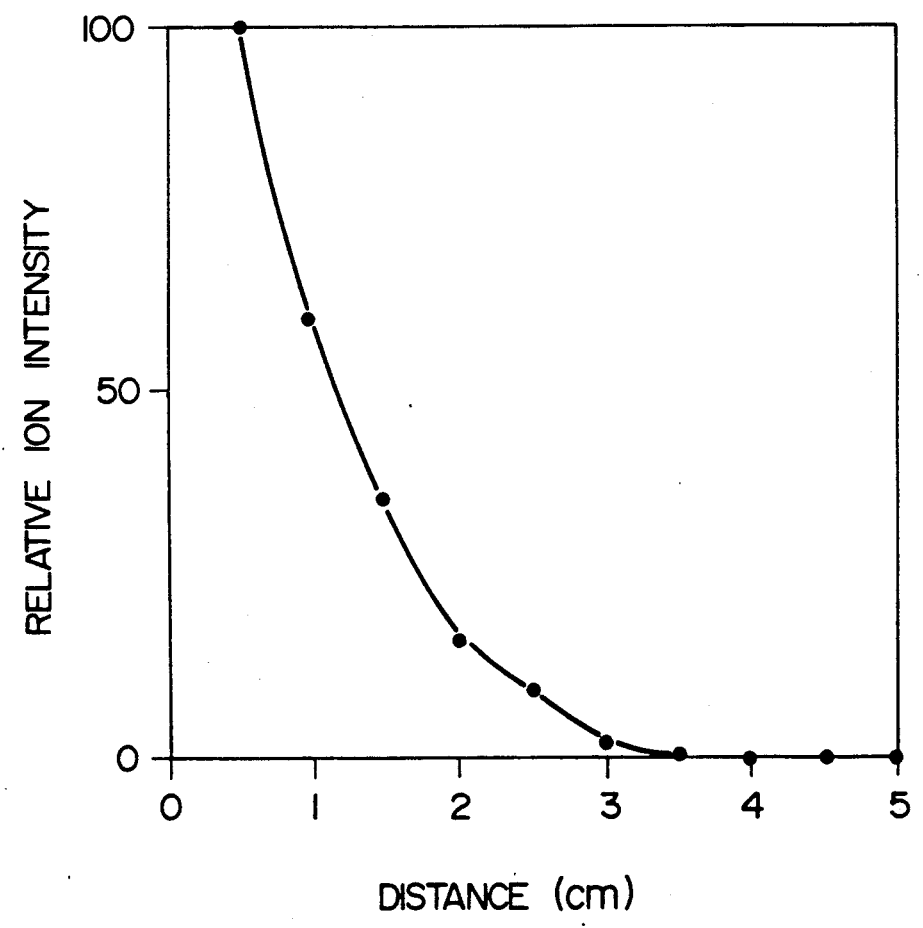
FIG. 6 is a diagram showing changes in the ion intensity of sucrose molecule ion $(M+Na)^+$ (molecular weight: 365) by changing distances between the tip end of metallic capillary and a first aperture in a thermospray mode.
Figure 16:
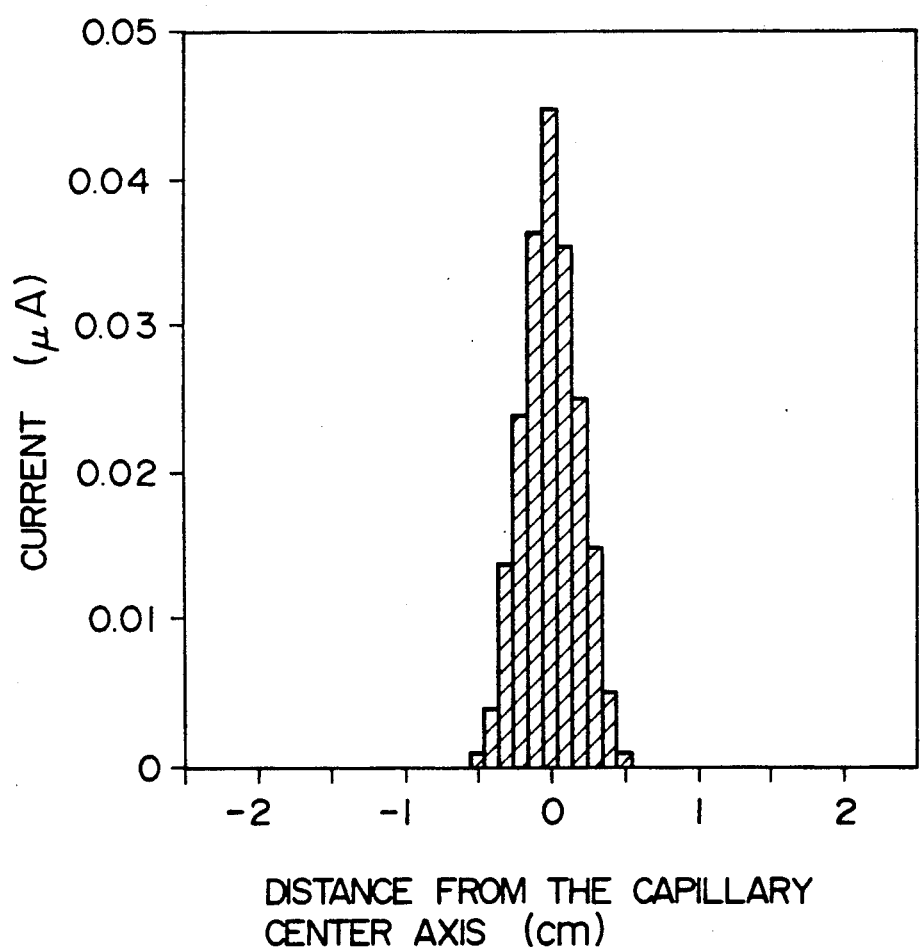
FIG. 16 is a diagram showing changes in the current by changing distances from the center axis when ions generated in a thermospray mode are detected by an electrode having a width of 1 mm at a position 10 mm distant from the tip end of capillary under the atmospheric pressure.

The thus generated ions can be efficiently introduced into the mass analyzing region and the vaporized sample molecules can be ionized by corona discharge under the atmospheric pressure according to embodiments shown in FIGS. 4 and 5. The radial distribution of ions sprayed from the capillary 11 is as shown in FIG. 16. That is, the amount of ions is larger near the center axis, and smaller toward the peripheral side. In order to efficiently introduce the ions into the mass analyzing region, it is necessary to align the aperture 14 along the center axis of capillary 11. The amount of ions is changed by changing distances between the tip end of capillary 11 and the aperture 14, as shown in FIG. 6. That is, the most preferable distance between the tip end of capillary 11 and the aperture 14 is not more than 1 cm, because a sufficiently large amount of ions can be obtained. Even if the distance is not more than 3 cm, a still sufficient amount of ions can be obtained. If the distance is more than 3 cm, the amount of ions to be generated is decreased to 1/10–1/20 of that when the distance is 1 cm, and this is not practical.

Figure 7:
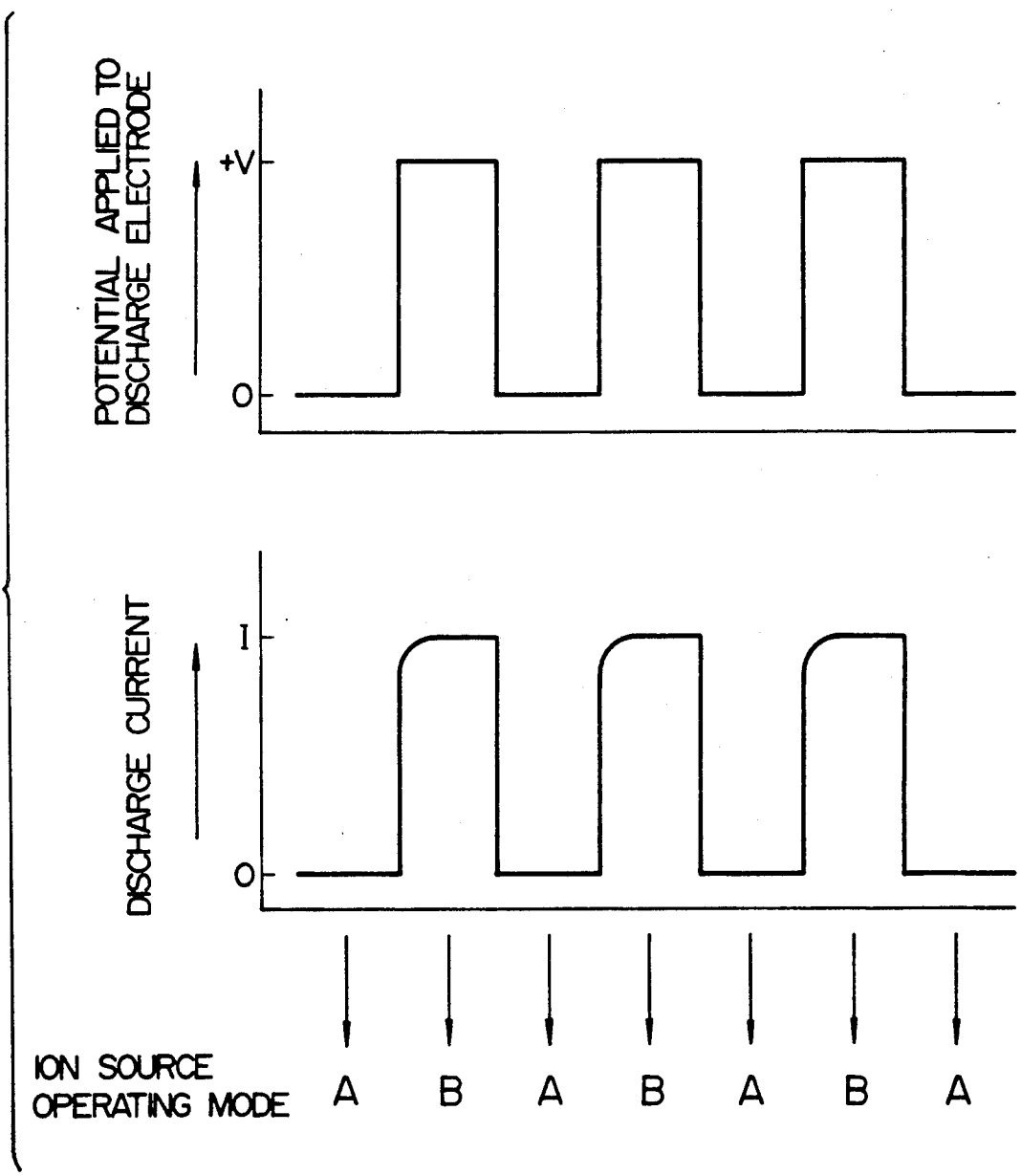
FIG. 7 is diagrams showing a relationship between the potential applied to a discharge electrode and the discharge current.

On the other hand, it is efficient to provide the discharge part of corona discharge electrode at a position 3–5 mm distant from the aperture. That is, the discharge electrode is so placed in the ion source as to be inserted between the capillary 11 and the first aperture 14, and the capillary potential is made equal to or higher than that of discharge electrode. As a corona discharge electrode, an ordinary needle 13 [FIG. 4(a)], a wire 19 [FIG. 4(b)], wires or wire mesh 20 [FIG. 4(c)], a wire 19 directly fixed to the capillary 11 [FIG. 4(d)], etc. can be used. When only a mass spectrum by corona discharge is desired, the capillary part must be at a lower potential than that of discharge electrode. Needless to say, ions can be formed and observed by the thermospray method without applying a potential to the discharge electrode, that is, without generating a corona discharge. Furthermore, the thermospray mode (case A) and the atmospheric pressure ionization mode (case B) can be alternately occasioned by applying a potential at a predetermined frequency to the discharge electrode or not, as shown in FIG. 7.

In order to detect the ions generated by the atmospheric pressure ionization method and the ions generated by the thermospray method at the same time, it is necessary to ionize the outside components of the jet injected from the capillary by an electric discharge and allow the center components to utilize the ions directly formed by spraying from the capillary, as shown in FIGS. 5(a) and (b), or to elevate the potential at the tip end part of capillary 11, provide an auxiliary electrode 23 having a higher potential than that of the capillary and allow the ions formed at the tip end part of capillary 11 to reach the first aperture 14 without any deviation to be caused by the potential of discharge electrode 19, as shown in FIGS. 5(c) and (d).

The embodiments shown in FIGS. 5(a) and (b) are such cases that an electric discharge is occasioned at the edge 21 of auxiliary electrode 23 provided at the tip end part of metallic capillary 11 or at a plurality of needles 22 fixed to the auxiliary electrode 23 to generate ions by the atmospheric pressure ionization method together with the ions formed at the tip end part of capillary. A mass spectrum is obtained for the whole of these ions. Embodiments shown in FIGS. 5(c) and (d) are such cases that a discharge electrode such as a wire 19, etc. is provided at the center in contrast to FIGS. 5(a) and (b) and an auxiliary electrode 23 is so provided as to focus the electric field into the direction of the first aperture 14 instead.

It is also possible to provide a wire 19, etc. at the center, as shown in FIG. 5(c), make the potential of wire 19 sufficiently higher than that of the first aperture 14 and control the temperature of capillary 11, thereby obtaining an ion field emission effect at the tip end of wire 19.

The thus formed ions are introduced into the vacuum in the mass analyzing region through the aperture 14 of a first electrode supported at an electrode support block 24 (see FIG. 1) and the aperture 15 of a second electrode supported at an electrode support block 25 provided with a pumping outlet. An insulating plate 26 such as ceramics, etc. is provided between the electrode support block 24 and the electrode support block 24 provided with the pumping outlet to attain an electrical insulation therebetween and also to allow a potential to be applied between the two blocks 24 and 25 and evacuate the space between the two blocks 24 and 25 to a pressure of a few Torr or less through the pumping system at the same time. The potential applied between the two blocks is to accelerate clustor ions formed by adiabatic expansion when the ions are introduced through the aperture of first electrode 14, thereby occasioning collisions with neutral molecules and splitting clustor ions which are inconvenient for the mass analysis. The ions which have passed through the first aperture 14 and second aperture 15 are mass analyzed by a double focusing mass spectrometer comprising an electric field analyzing section 4 and a magnetic field analyzing section 5 and detected by an ion detector 6.

Figure 8:
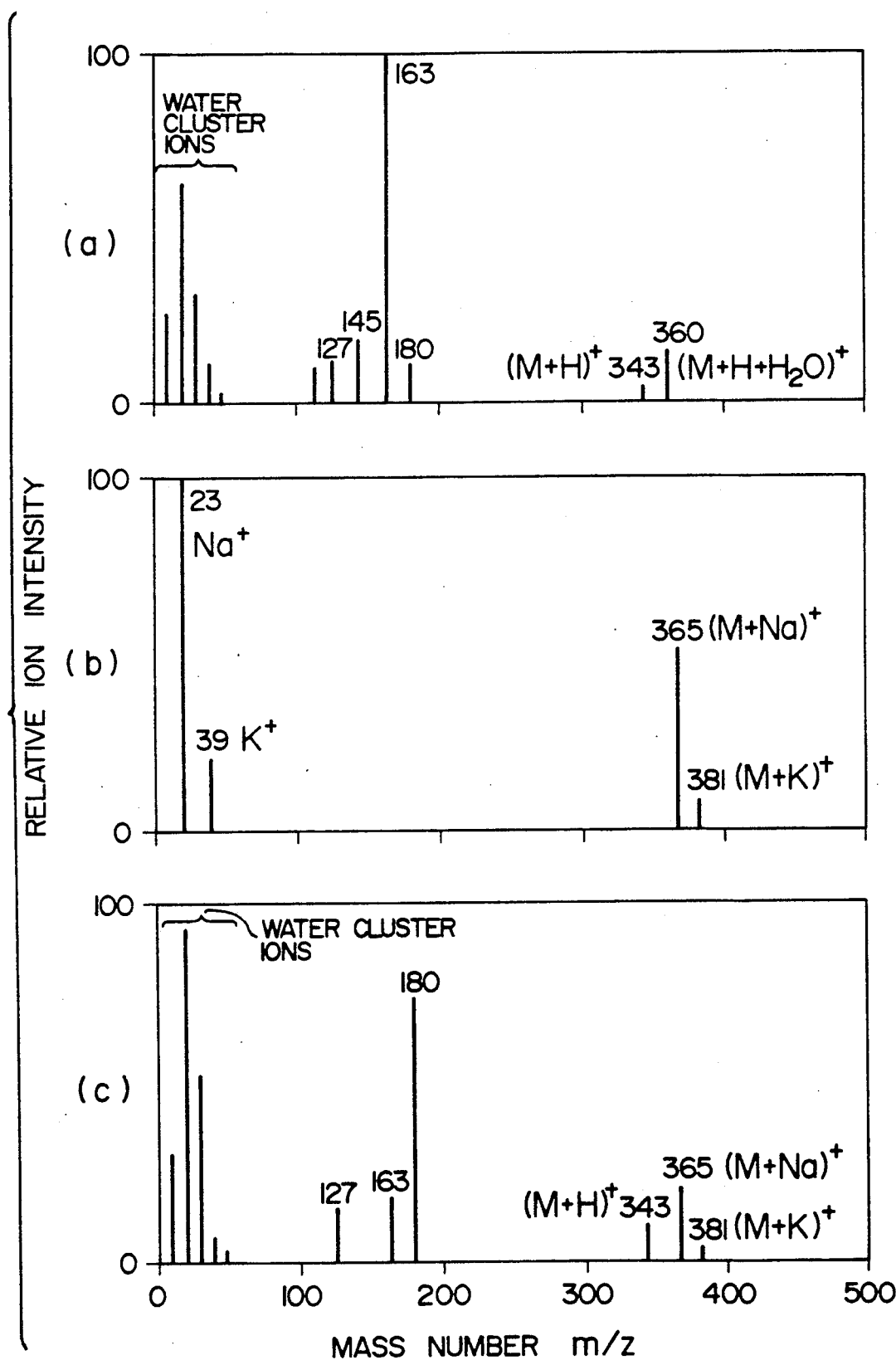
FIG. 8 is diagrams showing sucrose mass spectra.

In FIG. 8, mass spectra of sucrose (molecular weight: 342), a readily heat-decomposable compound, obtained by a conventional atmospheric pressure ionization method [FIG. 8(a)], a conventional thermospray method [FIG. 8(b)] and the present invention [FIG. 8(c)] are shown, where water is used at a flow rate of 1 ml/min. as a mobile phase in the liquid chromatograph, and discharge current is 5 $\mu$A during the electric discharge. In the mass spectrum by the atmospheric pressure ionization mode [FIG. 8(a)], fragment ions (mass number: 163) formed by breakage of molecules, cluster ions of solvent molecule, etc. are observable besides the proton $H^+$-adducted molecule ion species $(M+H)^+$ (mass number: 343). In the mass spectrum by the thermospray mode [FIG. 8(b)], molecule ion species $(M+Na)^+$ (molecular weight: 365) and $(M+K)^+$ (molecular weight: 381), adducted with alkali metals such as sodium Na or potassium K contained in the water as the mobile phase in the liquid chromatography are only observable besides sodium ions (mass number: 23) and potassium ions (mass number: 39), and fragment ions are not observable substantially at all. On the other hand, when the ions formed by the atmospheric pressure ionization method and ions formed by the thermospray method are detected at the same time according to the present invention [FIG. 8(c)], a mass spectrum like a total of the mass spectrum of ions by the atmospheric pressure ionization method and that of ions by the thermospray method can be obtained, and $(M+H)^+$, $(M+Na)^+$, $(M+K)^+$, etc. are observable as molecule ions.

Thus, the mass spectrum obtained according to the present invention has the following mass spectral characteristics, which are different from those of the mass spectrum by the thermospray method already reported.

Figure 9:
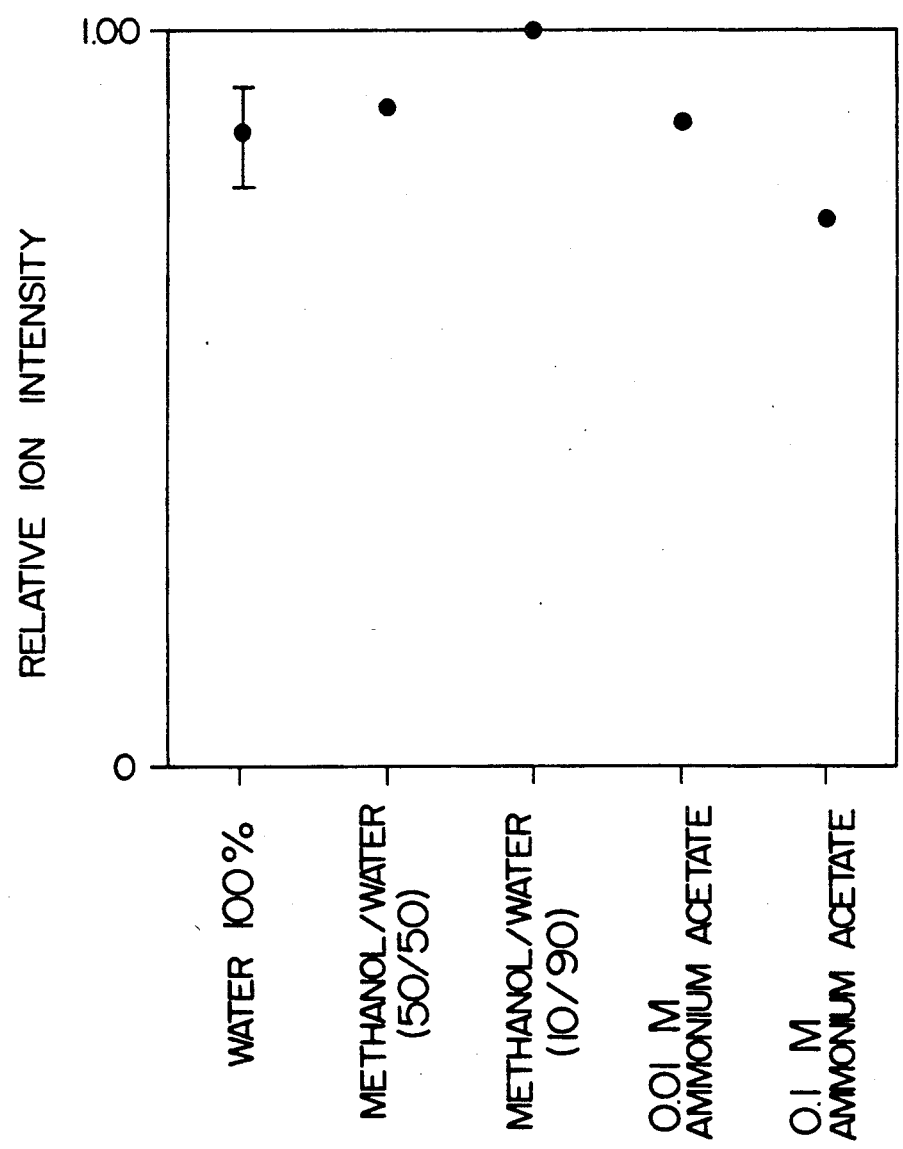
FIG. 9 is a diagram showing changes in the molecule ion intensity by different kinds of mobile phase used in the liquid chromatograph.

(1) In the conventional thermospray method, electrolytes such as ammonium acetate, etc. are required for obtaining molecular ions, whereas in the present ion source the molecular ion intensities are not dependent upon the amount of ammonium acetate and are observable even in water or with a mixture with methanol. In FIG. 9, comparison of ion intensities of sucrose quasi-molecular ions [M+Na]+ (molecular weight: 365) obtained with the present ion source is made among 100% water, water/methanol (50/50), water/methanol (10/90), aqueous 0.01M ammonium acetate solution and aqueous 0.1M ammonium acetate solution as mobile phases in the liquid chromatograph.

The ion intensities are less dependent upon the species of the mobile phase in case of the present ion source, and thus the present ion source is convenient for using the analyzing conditions for the liquid chromatograph.

(2) Molecular ions adducted with an alkali metal can be stably obtained by adding an alkali metal, etc. to the mobile phase.

(3) In the thermospray method, multiply charged ions such as doubly or triphy charged ions, which are inconvenient for the analysis, are readily formed, whereas in the present invention the multiply charged ions are less formed and the mass spectrum is simplified so that the interpretation of the spectrum can be facilitated.

Figure 10:
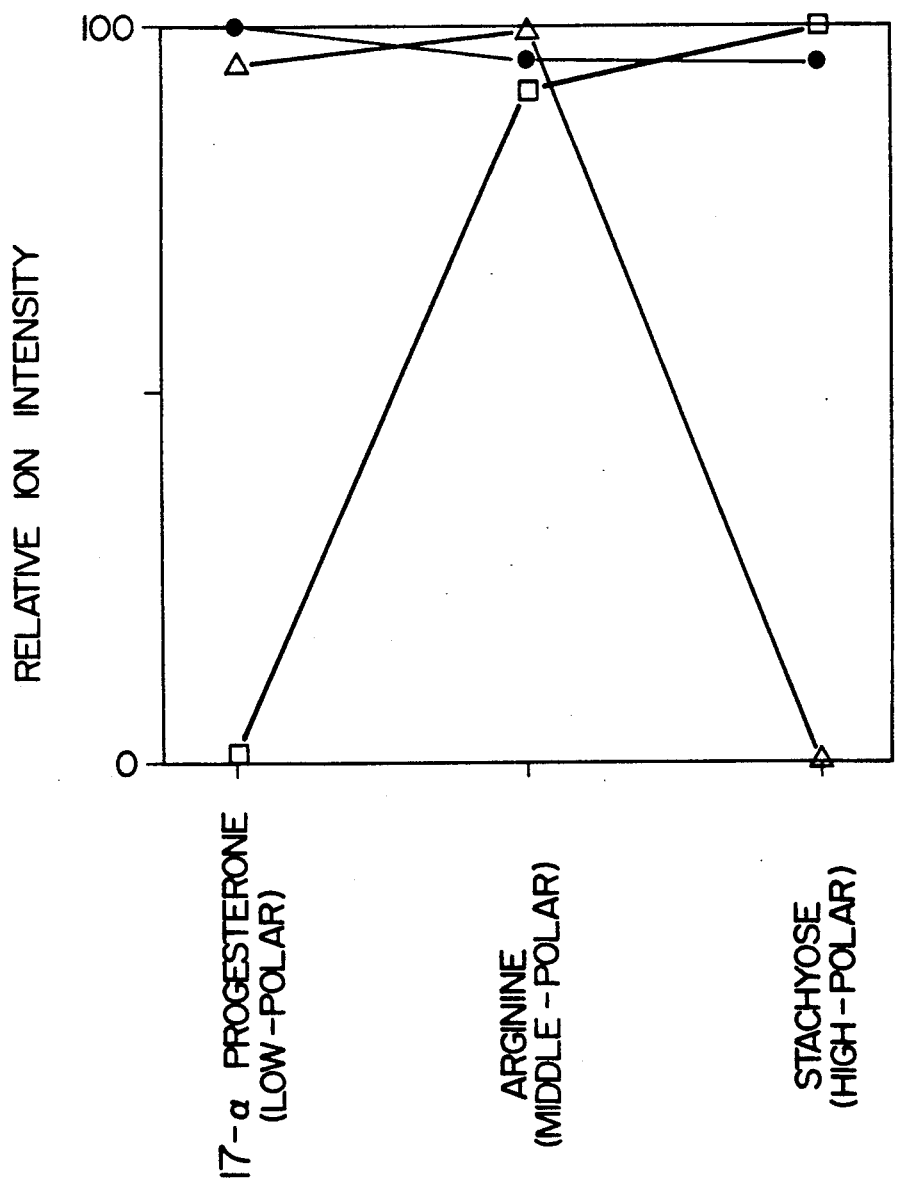
FIG. 10 is a comparative diagram of molecular ion intensities of 17-α-progesteron, arginine and stachyose according to a conventional atmospheric pressure ionization method, a conventional thermospray method and the present invention based on the integration of atmospheric pressure ionization method and thermospray method.
Figure 11:
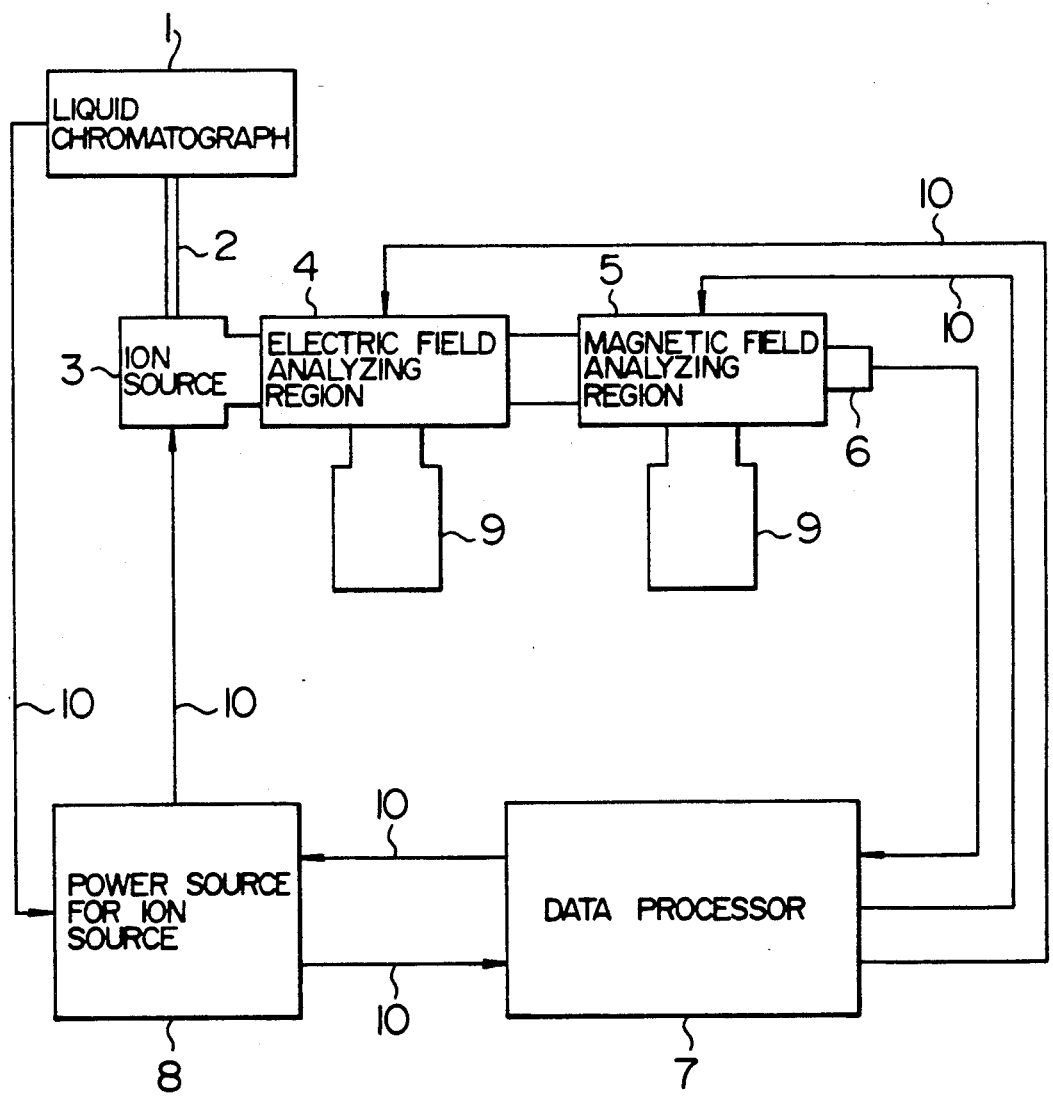
FIG. 11 is a flow diagram showing the structure of ordinary liquid chromatograph/mass spectrometer.
Figure 12:
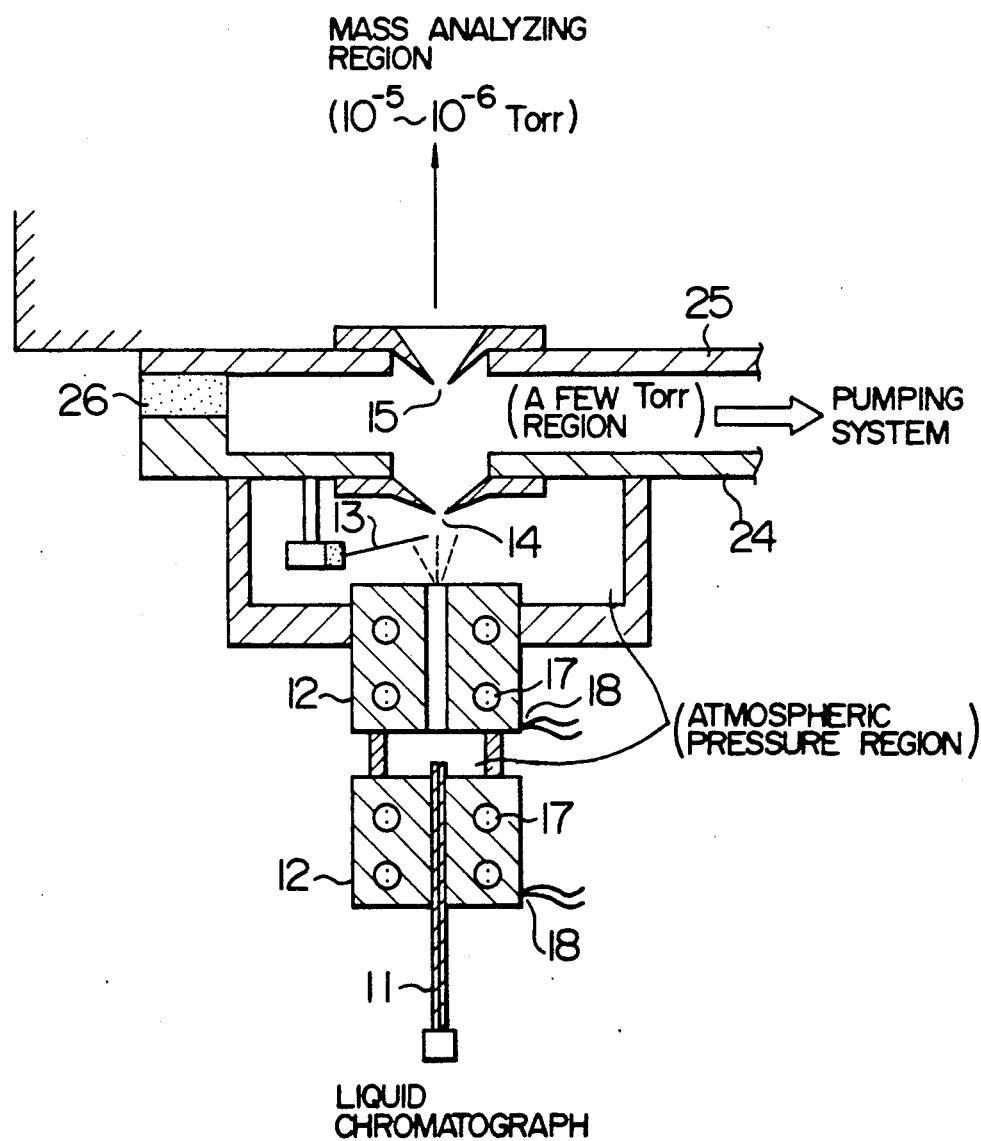
FIG. 12 is a schematic view showing the structure of the ion source of a conventional atmospheric pressure ionization method.
Figure 13:
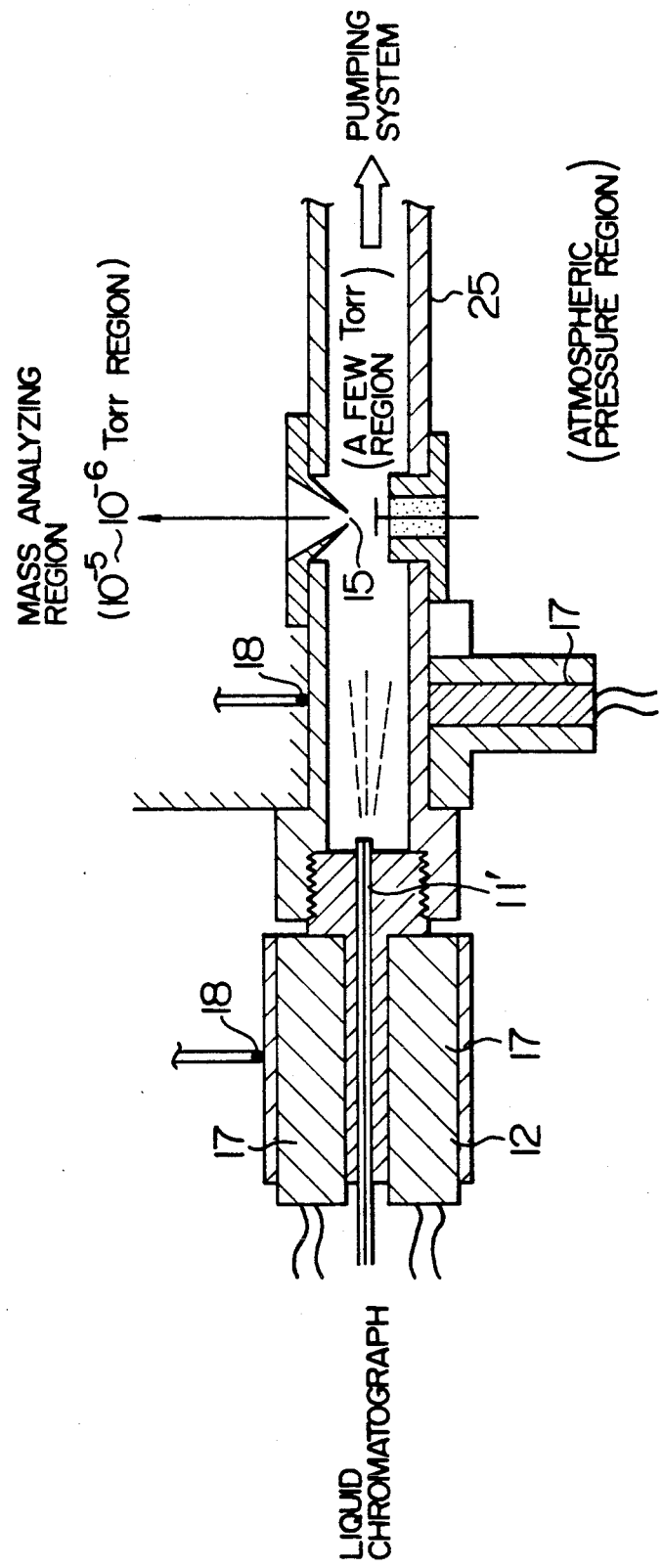
FIG. 13 is a schematic view showing the structure of the ion source of a conventional thermospray method.
Figure 14:
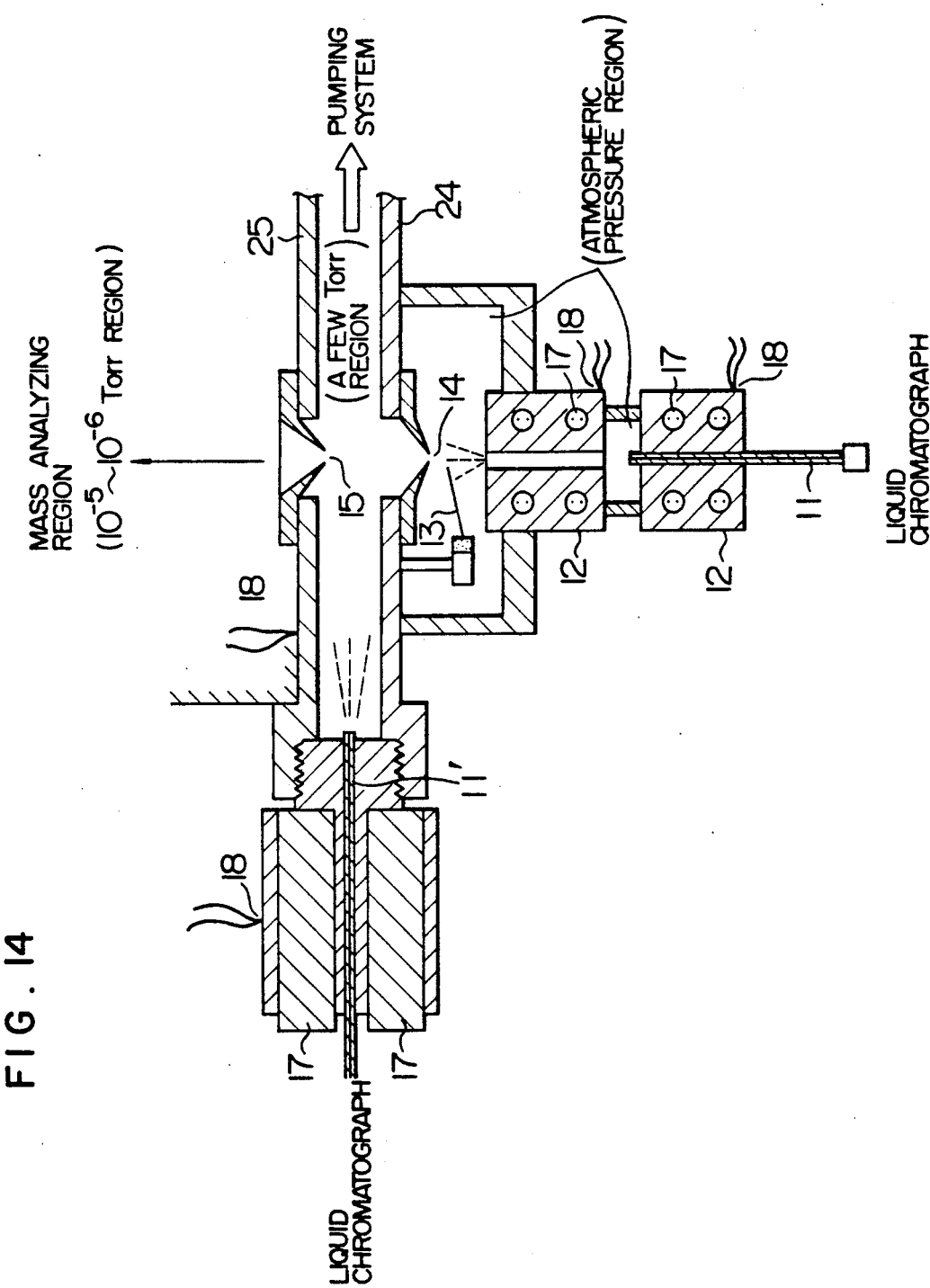
FIGS. 14 and 15 are schematic views showing the structure of a combined ion source of the atmospheric pressure ionization method and the thermospray method.
Figure 15:
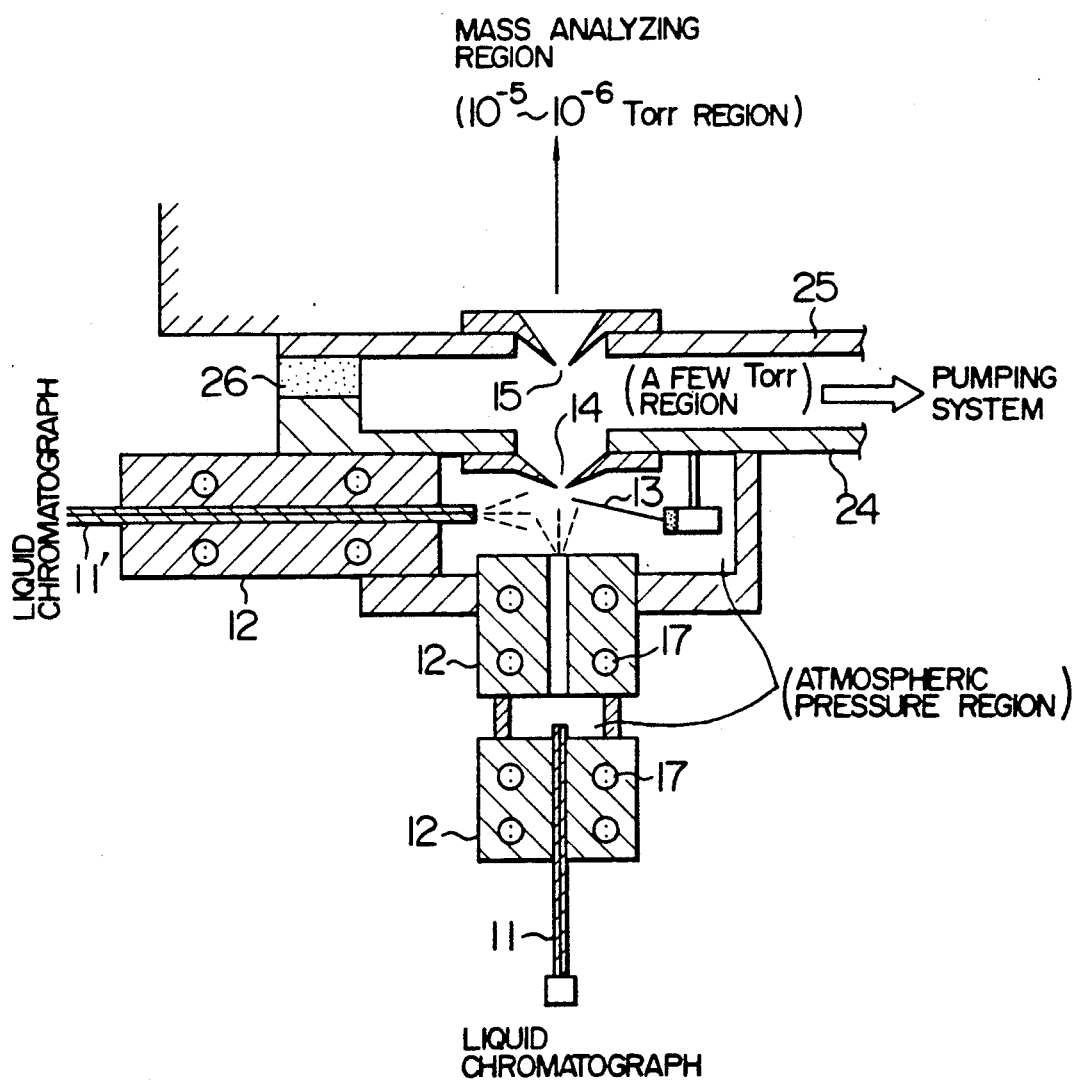

(4) In the conventional thermospray method, only high-polar compounds are measurable and in the conventional atmospheric pressure ionization method only low-polar compounds are measurable, whereas in the present novel, integrated ion source of the atmosphonic pressure ionization and thermospray methods, all the compounds are measurable, irrespective of the polar intensity. In FIG. 10, comparison of molecular ion intensities of 17-α-progesterone (a less high-polar steroid) arginine (a kind of a little high-polar amino acid) and stachyose (a particularly high-polar sugar) is made among the present invention, the conventional atmospheric pressure ionization method and the conventional thermospray method. As is apparent from the results shown in FIG. 10, the particularly high-polar sugar is hard to measure according to the atmospheric pressure ionization method and the less high-polar steroid is hard to measure according to the thermospray method, whereas the molecular ion intensities of all these compounds can be measured with a higher intensity according to the present invention.

As is apparent from the foregoing description, two ion sources for the atmospheric pressure ionization method and the thermospray method are integrated into one novel ion source working under the atmospheric pressure in the present invention, and (1) an applicable range to important non-volatile compounds relating to a living body can be much broadened, (2) a continuous operation can be carried out for a long time without providing any trap in the pumping system as in the conventional thermospray method and (3) it is not required to introduce a large volume of gas into the vacuume and thus contamination of the inside of ion source can be reduced when the mass spectrometer is provided with the present novel ion source.

What is claimed is:

1. A mass spectrometer which comprises an ion source of ionizing a sample and a mass analyzing region for introducing the thus formed ions into a vacuum and mass analyzing the ions, the ion source being provided with a thermospray ion source comprising a heatable capillary working at least at substantially atmospheric pressure, means for heating the heatable capillary, the center axis of the capillary being aligned along the center of an aperture for withdrawing the ions, and the tip end of the capillary being positioned close to the aperture, wherein the distance between the tip end of the capillary and the apertures is not more than 3 cm.

2. A mass spectrometer according to claim 1, wherein a corona discharge electrode is provided between the spray ions source and the aperture for withdrawing the ion.

3. A mass spectrometer according to claim 2, wherein a potential is pulsewise applied to the corona discharge electrode, and the ions formed by spraying and the ions formed by ion-molecule reactions following electric discharge are alternately withdrawn through the aperture.

4. A mass spectrometer according to claim 1, wherein the capillary is divided into a plurality of parts, and the individual parts are heated by the heating means and temperature controlled separately, thereby heating the capillary.

5. A mass spectrometer according to claim 1, wherein the sample is contained in an eluate from a liquid chromatograph.

6. A mass spectrometer according to claim 1, wherein the capillary is a metallic capillary.

7. A mass spectrometer which comprises an ion source for ionizing a sample and a mass analyzing region for introducing the thus formed ions into a vacuum and mass analyzing the ions, the ion source being provided with a spray ion source comprising a heatable capillary working at least a substantially atmospheric pressure, the center axis of the capillary being aligned along the center of an aperture for withdrawing the ions and the tip end of the capillary being positioned close to the aperture, wherein a corona discharge electrode is provided between the spray ion source and the aperture for withdrawing the ions, and wherein an auxiliary electrode for focusing the ions into the direction of the aperture is provided between the corona discharge electrode and the capillary.

* * * * *